United States Patent [19]

Kadokami et al.

[11] Patent Number: 5,695,971
[45] Date of Patent: Dec. 9, 1997

[54] PHAGE-COSMID HYBRID VECTOR, OPEN COS DNA FRAGMENTS, THEIR METHOD OF USE, AND PROCESS OF PRODUCTION

[75] Inventors: Yoichi Kadokami; Randolph V. Lewis, both of Laramie, Wyo.

[73] Assignee: Amresco, Solon, Ohio

[21] Appl. No.: 418,194

[22] Filed: Apr. 7, 1995

[51] Int. Cl.⁶ .............................. C12N 15/00; C12N 1/20; C07H 21/04
[52] U.S. Cl. .................. 435/172.1; 435/252.33; 435/320.1; 935/52; 935/55; 935/56; 935/58; 935/73; 536/24.1; 536/24.2
[58] Field of Search ............... 435/172.1, 252.33, 435/320.1; 935/52, 55, 56, 58, 73; 536/24.1, 24.2

[56] References Cited

U.S. PATENT DOCUMENTS 4,680,264  7/1987  Puhler et al. ................. 435/172.3
5,075,227  12/1991  Hagen ........................ 435/172.3

OTHER PUBLICATIONS

Watson et al., "Molecular Biology Of the Gene", 1965, pp. 210–211.

Shizuya et al., "Cloning And Stable Maintenance of 300-Kilobase-Pair Fragments Of Human DNA in *Escherichia coli* Using An F-Factor-Based Vector", Proc. Natl. Acad. Sci, USA, vol. 89, Sep. 1992, pp. 8794–8797.

Chauthaiwale et al., "Bacteriophage Lamboda As A Cloning Vector", Microbiological Reviews, Dec. 1992, pp. 577–591.

Zuber et al., "Tn5cos: a transposon for restriction mapping of large plasmids using phage lambda terminase", Gene 103: 69–72, 1991.

Sambrook et al., "Molecular Cloning: A Laboratory Manual", 2nd edition, Cold Spring Harbor Laboratory Press, pp. 3.4, 2.42–2.43, 8.37–8.38, 3.28–3.31, E.34–E.36, 6.32–6.35, 2.85–2.87, and 2.12, 1989.

Enquist et al., Meth. Enzymol., pp. 281–298, 1979.

*Primary Examiner*—Mindy Fleisher
*Assistant Examiner*—Bonnie D. Weiss
*Attorney, Agent, or Firm*—Foley & Lardner

[57] ABSTRACT

A hybrid vector produced from a linearized cosmid and arms from λ phage vector DNA has been developed. The hybrid vector can be used to generate fragments which are useful as vectors in a helper phage-mediated transformation system, permitting large fragments of foreign DNA to be introduced into a host on an industrial scale.

22 Claims, 6 Drawing Sheets

PHAGE-COSMID HYBRID VECTOR, OPEN COS DNA FRAGMENTS, THEIR METHOD OF USE, AND PROCESS OF PRODUCTION

FIELD OF THE INVENTION

The present invention is directed to a hybrid vector produced from λ phage vector DNA and cosmid DNA, open cos DNA fragments, their use in a helper phage-mediated transformation system, and a method of producing same.

BACKGROUND OF THE INVENTION

In 1960, Kaiser and Hogness found that a lysogenic *E. coli* strain of λ phage could uptake λ phage DNA encoding a different repressor gene. This was done by infecting the same type of λ phage as helper phage in advance at high multiplicity of infection (m.o.i.), and the cells would allow the incorporated DNA to replicate and the cells to lyse (15) (the preceding and following numbers in parentheses are in reference to the numbered list of references contained at the end of the specification). This is known as helper phage mediated transformation (HPMT). Since 1960, HPMT has been improved and used to demonstrate the colinearity of the vegetative genetic map of λ with the physical sequence of genes along the DNA (16, 17, 18). The repressor is expressed in the lysogen and its protein inhibits the growth of the helper phage. However, once the external phage DNA, which encodes a different repressor, is incorporated and replicated, the cells lyse. Only λ phage DNA can be incorporated when λ phage is used as the helper phage. Subsequently, it was discovered that the lambdoid phages and P2 phage had the same effect, but the ends of the DNA to be incorporated must coincide with the helper phage, suggesting that the structure of the ends of the phage DNA ("cohesive" ends) are related to this phenomenon (19).

In 1981, Miller and Feiss demonstrated how cells infected with the helper phage could incorporate the additional phage DNA (20). The authors designed the experiments to prove this function using cos-open cosmid DNA which was cut by the ter reaction in vitro. They could recover one type of hybrid DNA in circular form which consisted of full helper phage and cosmid DNA ligated at each cohesive ends. They made three models to explain this observation as follows:

1. Helper phage DNA molecules and free DNA molecules enter the cell without interacting and cyclize at random.
2. Cohesive end annealing between the helper phage and the free DNA is necessary for entry into the cell.
3. A high probability of cohesive end annealing between the free DNA and the helper phage might exist as a consequence of the proximity of the helper cohesive end(s) to the entry of the free DNA.

The first model is not likely because the formation of multimers by cohesive end annealing is rare, and the plasmids resulting from the experiments almost always contain the helper phage chromosome. The second model fits their results. However, the possibility of the third model cannot be excluded. They also pointed to two types of plasmid instability; defective segregation and plasmid breakdown. The former may simply be due to a low copy number of the recombinant, and the latter may occur by a recA-independent recombination.

λ DNA is linear when it is in a capsid, but once the phage infects *E. coli* cells, packaged DNA is injected into the cells uncovering the termini (i.e., cohesive ends) to be circularized for DNA replication, transcription, and translation. The cohesive ends of linear λ phage DNA are self-complementary, extruding 12 bases (or nucleotides) and facilitating circularization after infection. The *E. coli* host strain, which is a λ lysogen, can adsorb λ phage at a high multiplicity of infection (super-infection, m.o.i.=10) without lysis because the lysogen produces phage-specific repressor proteins (cI repressor) which repress the expression of phage operons. Usually, 10 to 20 molecules of repressor protein are produced in a lysogenic strain.

λ phage needs λ receptors on the membrane to adsorb to *E. coli* cells. This phenomenon determines the host specificity, and the receptor is encoded on the *E. coli* chromosome (lamB). Adsorption can be attained in a few minutes even at 0° C., and it can be maintained without injecting DNA into the cell when the cells are incubated at 0° C. Adsorption is a reversible reaction, and follows a Poisson distribution because only spontaneous molecular collisions between λ phage tails and receptor proteins determine efficiency. With a short incubation above 15° C., but at permissive temperatures, simultaneous DNA injection from the phage heads into the cells takes place and the DNAs remain temporally between the outer and inner membranes (periplasmic space). This state can be maintained for at least 5 hrs at 0° C. Flip-flop of injected linear phage DNA occurs on the outer membrane while in this state, resulting in the cohesive end of phage DNA extruding frequently through the outer membrane, thereby trapping any external DNA having cohesive ends (e.g., a foreign DNA segment desired to be introduced into the host) by annealing. A temperature shift from 0° C. to 30° C. or 37° C. allows the DNA to be drawn into the cytoplasm. The authors (20) designed an experiment to prove this function using cos-open cosmid DNA which was cut by the ter reaction in vitro. The mechanism of introducing the injected phage DNA is not known, but the host mutant (pel-) does not allow DNA injection from phage particles (21). Host factors may play an important role in the process. The overall process is illustrated in FIG. 1.

The ter reaction was constructed by Becker and Gold isolating the key enzyme, pA (terminase) (22), and the in vitro system is commercially available as a kit (LAMBDA TERMINASE™, Gibco BRL). However, since the reaction requires unknown *E. coli* factors, the reaction is not as efficient as other single enzyme reactions, which makes duplication difficult. Since this ter reaction was the only way to produce the open cos arms from the cosmid, application of this method for general cloning purposes was not indicated by the authors and, in fact, was actually impossible at that time.

More recently, cloning of long DNA segments has become important in the construction of gene libraries and analysis of very long genes, especially those of the eukaryotic genomes. It has become clear that many genes are too long to be clones as single fragments in standard vectors. The bithorax and antennapedia of Drosophila, for example, contain transcription units of 75 and 100 kb (1,2,3,4), respectively. The human factor VIII is 180 kb (5), and dystrophin's transcription unit is the longest found to date (1,800 kb) (6). The ultrabithorax (Ubx) gene is regulated by sequences located upstream (50 kb) and within the introns (7). And although a gene such as the human β-globulin gene has a transcription unit of only few kb, sequences as far as 50 kb upstream appear necessary to obtain full expression in transgenic mice (8). Thus, the ability to clone large DNA segments containing relatively small genes is important.

These large functional units of DNA need to be manipulated and cloned efficiently. In most cases, to examine the functions of cloned segments, DNAs can be delivered into the eukaryotic cells with or without the vector. Transfection of cultured mammalian cells requires no special vector but marker genes are usually needed, e.g., the thymidine kinase gene for work with mammalian cells, suppressor tRNA genes for transformation of nematodes, and G418 for P-element mediated transfection into Drosophila cells (9,10). Most of these genes were isolated from libraries constructed in phage vectors which can clone inserts up to 24 kb in size, or in cosmid vectors which are useful up to 45 kb in length (11).

Large regions of the genome are usually cloned in a series of overlapping recombinants isolated by chromosome walking. A segment of non-repetitive DNA isolated from one end of a recombinant is used as a probe to screen recombinant clones containing adjacent sequences. This process is repeated until the entire region has been covered. This method requires an extraordinary amount of time and labor. Recently, a P1 phage vector and its in vitro packaging system were developed and the technique could reach a cloning range of 100 kb in $E.\ coli$ (12). However, undesirable size restrictions are associated with this system.

The YAC system was developed based on the creation of extra chromosomes introducing telomeres in yeast (13). In addition, the vector has two small units that function as a centromere and as a replication origin (ARS element). This technique allows the cloning of much larger segments of DNA, up to several hundred kb, but the yeast chromosomes are more difficult to handle than bacterial plasmids due to their linear configuration, which can be sheared during manipulation. Screening clones from yeast colonies is more difficult than from $E.\ coli$, and isolating the target DNAs from the positive clones requires special techniques, necessitating more restrictions during manipulation than when $E.\ coli$ is used.

Shizuya et al. (4) introduced a new $E.\ coli$ cloning system based on an F-factor vector (BAC). They achieved cloning of DNA up to 300 kb, demonstrating the stability of cloned DNA and ease of its manipulation because existing passenger DNA is the form of a supercoiled circular plasmid. However, since this method depends on electroporation, long DNA cannot be incorporated into cells as easily.

Therefore, a system for $E.\ coli$ cells is still needed for the cloning of large DNA segments at high efficiency and which is easy to use. The present inventors have discovered such a system as hereinafter described.

DETAILED DESCRIPTION OF THE INVENTION

Figure 1:
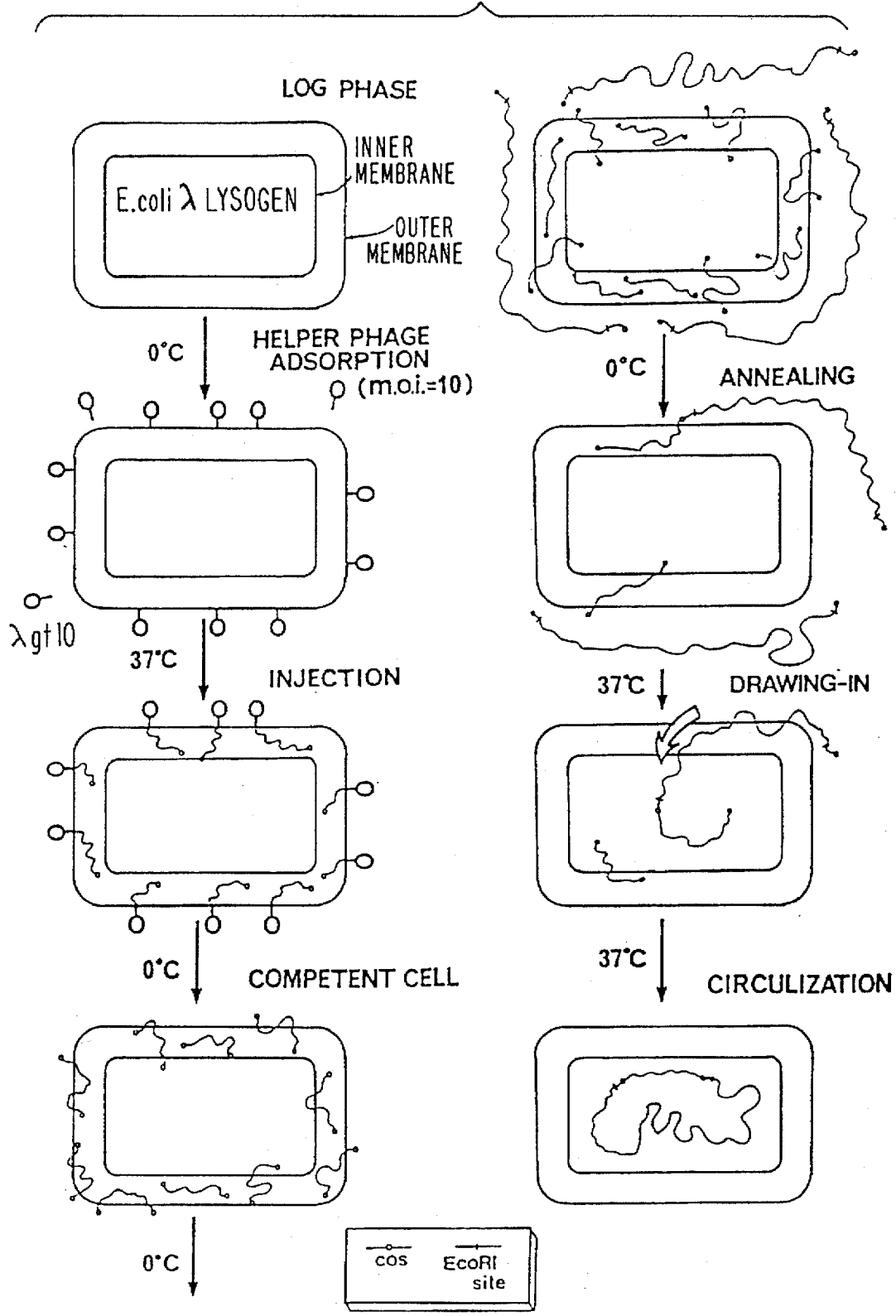
FIG. 1 shows the general method of helper phage-mediated transformation (HPMT).

One embodiment of the present invention is a hybrid vector comprising a linearized cosmid having a single unique restriction enzyme site between 2 marker genes, wherein the linearized cosmid is ligated between left and right arms produced from digestion of λ phage DNA. The vector is useful for producing arms having open cos ends that can be used to transform a bacterial host with large segments of foreign DNA on an industrial scale. A preferred hybrid vector is λKAD93.4, which is a hybrid phage prepared from λgt11 and pHC79 cosmid DNA.

A second embodiment of the present invention is a method of transforming a bacterial host with a foreign DNA sequence comprising the steps of:

digesting λ phage vector DNA with a restriction enzyme to generate a left arm and a right arm, linearizing a cosmid vector with the restriction enzyme to produce linearized cosmid DNA, ligating the linearized cosmid DNA between the left and right arms to produce a hybrid phage-cosmid vector, packaging the hybrid phage-cosmid vector into phage heads in vitro, infecting a bacterial cell with the phage particles to propagate the phage particles thereby forming phage plaques, transferring the plaques onto a membrane, screening the hybrid phage-cosmid vector from the membrane by hybridizing with a DNA probe, preparing a phage lysate by infecting the hybrid phage-cosmid vector to the host bacterial cell, precipitating the cell debris from the lysate, removing the bacterial cell's DNA and RNA by nuclease treatment, precipitating the propagated phage particles, extracting the packaged DNA from the precipitated phage particles, digesting the extracted DNA with the restriction enzyme to generate a mixture of DNA fragments, isolating the shortest two fragments from the mixture of fragments which are DNA fragments bearing an open cos site on one end, ligating a foreign DNA sequence between the two open cos site fragments, and transforming a host bacterial cell with the ligated foreign DNA sequence having the two open cos sites using a helper phage-mediated transformation system.

The restriction enzyme used in the above method is selected according to the type of vector used. A preferred restriction enzyme is EcoRI when λgt11 is used.

The marker genes can be any conventionally used marker gene known to those of ordinary skill in the art. Preferred marker genes are antibiotic resistance genes. Particular preferred marker genes are $amp^r$ and $tet^r$, encoding ampicillin and tetracycline resistance, respectively.

Still another embodiment is a bacterial host transformed with a desired segment of foreign DNA ligated between the open-cos arms produced from the hybrid vector, wherein transformation is effected using the helper phage-mediated transformation system.

Still another embodiment is a purified DNA fragment comprising an open cos site on one end and a restriction enzyme site on the other end. Preferably, the fragment is up to about 3.3 kb in length. A preferred cos site has the sequence 5' GGGCGGCGACCT 3' (SEQ ID NO:1). A preferred restriction enzyme site is EcoR1. Preferably, the purified DNA fragment further comprises a marker gene to facilitate identification and maintenance.

The foreign DNA sequence desired to be introduced into the bacterial host cell can be any DNA sequence up to about 5 megabases (Mb) in length, more preferably, up to about 1 Mb in length. For example, suitable foreign DNA sequences may be produced from genomic DNA that has been digested with a suitable restriction enzyme or exonucleases and fractionated. Any known method for preparing DNA fragments can be used to produce a foreign DNA sequence that may be introduced into the bacterial host cell using the method of the present invention.

Any vector of λ phage permitting the introduction of a piece of DNA may be used as the source of DNA for the hybrid vector. A preferred strain of λ phage is λgt11 whose unique cloning site is for EcoRI.

Any cosmid vector may be used which is autoreplicable and contains a single unique restriction enzyme site, which is compatible with that of a λ phage vector, between 2 selective markers. Preferably, the cosmid vector comprises a set of unique restriction enzyme sites between 2 antibiotic resistance genes. Preferably, the cosmid contains short cosmid arms having a λ cos site at almost the same distance from the cloning site for easy fractionation. A short arms region derived from λDNA containing cos is preferred because they reduce the likelihood of homologous recombination and they are needed for in vivo phage packaging. Preferably, the cosmid is also a low copy and not a run-away type plasmid, which will increase the likelihood of homologous recombination. A preferred cosmid is pHC79.

As used herein, the term "cos site" means a sequence of the cohesive end of lambda and "cos end" or "open cos site" means a 5'-end overhang of λ DNA containing a 12 base sequence: 5' GGGCGGCGACCT 3' (SEQ ID NO:1). The cos site is created by the ter reaction including pA and pNu-1.

In the step of isolating the hybrid phage-cosmid vector from the membrane, any suitable DNA probe can be used which will bind to the DNA of the hybrid phage-cosmid vector. A preferred probe is a pHC79 DNA fragment. Other screening techniques known in the art can be used.

The host bacterial strain should be a stable lysogen, and the lysogenized phage should be blocked to prevent induction and repress expression of the super-infected helper phage. A shortage of repressor may induce the expression of the super-infected helper phage and cell lysis. Also, the host bacterial strain preferably has rec mutations or related mutations which minimize recombination. Also, the host bacterial strain should have a set of marker genes for easy maintenance and identification.

A preferred bacterial strain which can be used to construct a host strain for HPMT by infecting λind- is the SURE™ strain (available from Stratagene, La Jolla, Calif.) having two rec mutations: recB and J. Another preferred host bacterial strain is $E.$ $coli$ strain NS428 (λred) and NS433 (λred), which possesses λred and the recA mutation. Since the latter strain can be lysed at temperatures around 42° C., it should be grown at 30° C., which ensures slow growth and may reduce the level of recombination. In addition, any other lysogenic strain with λ phage and the rec mutations can be used.

Other preferred host bacterial strains include $E.$ $coli$ KD9302 and KD9402. The former strain has both recB and J mutations to repress recombination, F' with $tet^r$ as a genetic marker, and λind- in the genome, and the latter is the same as the former except F'. When the former strain is cultured in a medium with tetracycline, it is rarely lost due to segregation of F'. In addition, both strains are believed to have tandemly repeated λind- on their genomes, which is advantageous because it ensures the production of a sufficient amount of repressor.

As shown in FIG. 1, helper-phage mediated transformation involves lysogenizing $E.$ $coli$ cells with λ phage followed by infection with excess λ phage ("helper" phage) at mid log phase. When infection is carried out at 0° C., phage can adsorb on the cell surface reversibly. Then, a short incubation of the cells at a suitable temperature (around 30° to 37° C. depending on the type of host strain) allows DNA injection into the periplasmic space of the cells. This state can be held for several hours if the cells are kept on ice after phage adsorption. Alternatively, in a suitable medium, cells can be kept in the freezer for several months without loss of activity.

The injected helper phage DNA protrudes its ends bearing cos ends occasionally outside the surface of the outer membrane. This allows foreign DNA ligated between cosmid arms to be annealed to the cos ends of the helper phage by mixing with the cells at 0° C. In such a manner, the cos end of the helper phage can trap the complementary cos site from the foreign DNA. Subsequent incubation at a suitable temperature facilitates incorporation of the phage DNA into the cytoplasm with the annealed vector-plus-foreign DNA at the cos site. Although the mechanism is still not fully understood, proteins produced by $E.$ $coli$ are known to play an important role in this stage. This incorporation occurs independently of DNA size.

Once the phage DNA or foreign DNA hybrid has been incorporated into the cytoplasm, the hybrid can be circularized by annealing at both cos ends, and then ligated to start replication. Since the λ phage replication is blocked by the repressor produced by the lysogenic λ phage in the host strain, the attached replication origin of the cosmid allows replication of the hybrid DNA. The replication can be regulated by the ColE1/ori on one of the cosmid arms, while the copy number of the hybrid DNA can be regulated as well. The hybrid DNA can be amplified by addition of chloramphenicol prior to the DNA extraction in the same manner as other relaxed type plasmids. Preferably, a low copy number cosmid DNA is selected, which does not interfere with the chromosomal DNA of $E.$ $coli$ replication.

The invention is more clearly illustrated by, though in no way limited to, the following examples.

Construction of a Lysogenic Strain

To prepare the infective phage as the helper phage in this method, the titer must be as high as possible. The method utilizes multiplicity of infection (m.o.i. )=10 to prepare competent cells. Since a high concentration of the recipient cells is desirable to obtain a high transformation rate, the titer of the helper phage should exceed $10^{10}$ pfu/ml ("pfu" stands for plaque forming unit). Infection in broth cannot attain this value. Therefore, a new lysogen strain of $E.$ $coli$ was constructed as follows.

$E.$ $coli$ strain LE392 (e14⁻(mcrA) hsdR514 supE44 supF58 lacY1 or Δ(lacIZY)6 galK2 galT22 metB1 trpR55) and $\lambda_{cI857sam7}$. A fresh overnight culture of LE392 was poured onto a λ agar plate with phage ($\lambda_{cI857sam7}$) to make a confluent plate. The plate under these conditions is usually clear. But, if propagation is established by superinfection, some of the colonies appear on the plate. In such a way, 22 colonies were obtained, and after purification these were examined by infecting phage. All were resistant to the same phage, and the integrated phage was inducible at non-permissive temperature (42° C.). Since the repressor of the phage is temperature sensitive ($CI^{857}$), the lysogen must be grown at permissive temperature (30° C.). Then, the culture is shifted to non-permissive temperature to inactivate the repressor. After this treatment, cell lysis begins because the amber mutation of protein S (Sam7) is suppressed by two sup mutations (supE and supF). To get the highest titer of the phage, the culture is concentrated before induction rather than at the endpoint of induction as with other strains. The latter case sometimes lyses cells from inside because of high concentration of phage. This may lead to the loss of phage before cell lysis with chloroform. The titer showed $1 \times 10^{10}$ to $10^{11}$ pfu/ml.

Construction of a Host Strain

The strain NS428, which is a stable lysogen of λred, was used. As this strain is temperature sensitive, it is necessary to grow the cells at 30° C. which extended the doubling time. Especially, on the plate, the transformants grew extraordinarily slowly. To improve the cell growth, a new strain was constructed introducing better mutations. NS428 has a recA mutation to prevent recombination, but recA alone is not sufficient for the highly repetitive sequences which are common in the eukaryotic genomes. SURE cells (Stratagene) are well designed to maintain even Z-form DNA by introducing two rec mutations (recB and J). This strain was used to construct the lysogen. λind- was infected into SURE cells as described in the preceding section (Construction of a Lysogenic Strain), and the lysogens were isolated. Out of 12 clones, there were typically two groups, one of which was more sensitive to superinfection of the helper phage, and the other of which was quite stable for superinfection. Since λind- can be integrated in the genome tandemly, the latter group, which is believed to be a tandem λind- prophage, was selected.

Curing of KD9302 Strain

A new strain of *E. coli*, KD9302, was constructed and its ability for helper phage mediated transformation was tested. Transformation efficiency was the same as with NS428 discussed above. For small plasmid DNA, the presence of F' may not affect recovery of the target plasmid DNA. Since the helper phage mediated transformation aims at cloning extremely long DNA fragments in *E. coli* cells, the size of the cosmid DNA in the cells may compete with F' whose size range is from 70-150 kb. The method of cosmid extraction may also cause F' DNA contamination which would make identification of the target DNA difficult. Therefore, the curing of F' from the strain, KD9302, was carried out with three commonly used reagents: acridine orange, ethidium bromide and SDS.

Fifty μL of an overnight culture of KD9302 in MMB (27) was inoculated in fresh 5 mL of MMB containing 30 μg/ml acridine orange, 0.5 μg/ml ethidium bromide, and 10% SDS, respectively. Then the cultures were incubated overnight. Cultures containing acridine orange and ethidium bromide grew well, but SDS culture showed very poor growth. Each one was streaked on LB agar plate and incubated. Even though the growth of the cells in 10% SDS medium was poor, the plate gave enough colonies to be examined. From each plate, 50 colonies were transferred on both plain LB and LB agar plate containing tetracycline to examine tetracycline resistance. If F' is cured, tetracycline resistance is removed as well, because its gene is located on the F'. These plates were incubated overnight. From SDS treated cells, 3 colonies were isolated showing tetracycline sensitivity. From acridine orange treated cells, 1 colony was isolated. No colonies were formed on the ethidium bromide plate. These colonies were then inoculated in MMB and incubated overnight. The next day, cultures were streaked on Davis' minimal medium agar plates, one included proline and the other did not. Since proline is linked with tetracycline on the F' and the entire proline gene was deleted on the host strain, the cured strain should show proline dependence. All isolated strains required proline, proving that all strains were cured. Another advantage of these strains was that the cells could have two antibiotic resistance marker genes to make strain maintenance easier. The new strain was named as KD9402.

Production of Cosmid Arms from Hybrid Vector

A λ phage vector, λgtll, and cosmid DNA, pHC79 (available from Gibco BRL), were both digested with EcoRI. The hybrid vector was constructed with two cos sites, one on λgtll and the other on the cosmid. In the next step shown in FIG. 2, the linearized pHC79 DNA is ligated in between the right arm of λgtll and the left arm of λgtll, after which the hybrid DNA is packaged in vitro into phage heads (a kit for which is available from Gibco BRL). Because the packaged fraction is not homogeneous, self-ligated lambda phage is dominant in the fraction. This produces recombinants by a reaction in vitro.

Figure 2:
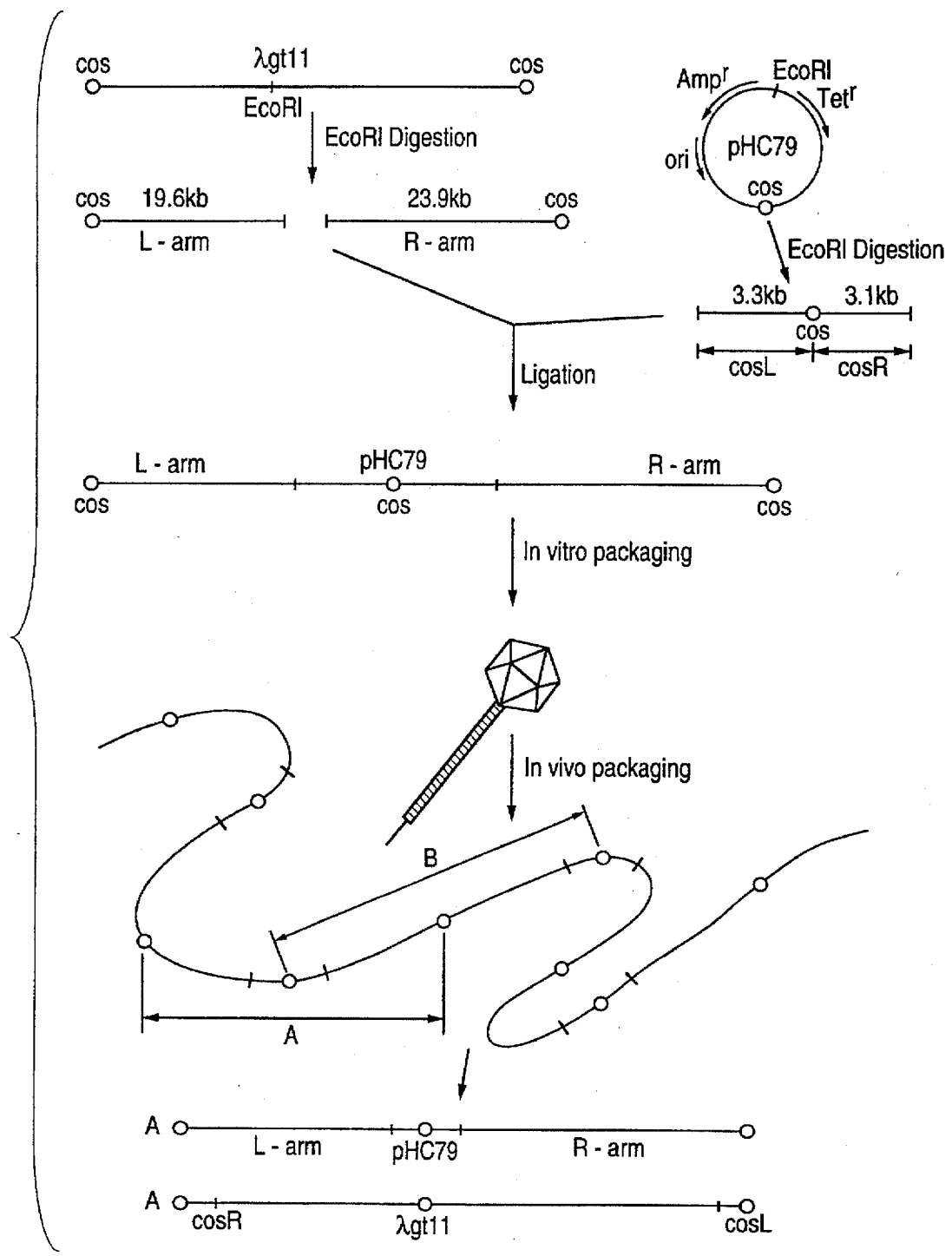
FIG. 2 shows the general method for producing a λ phage DNA-cosmid DNA hybrid vector of the present invention from λgt11 DNA and the cosmid pHC79.
Figure 3:
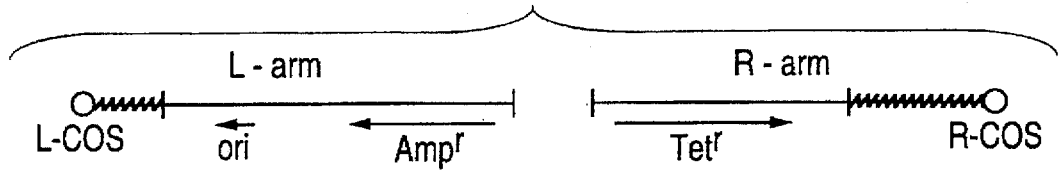
FIG. 3 shows the features of the L-arm and R-arm.

When the host strain is infected with the packaged phage particles, two types of hybrid DNA are made in vivo as shown in FIG. 2. The hybrid DNA vector can be packaged in two different ways using cos sites derived from either λgtll or pHC79. As shown in FIG. 2, the resulting population of the hybrid phage includes both forms, denoted A and B in FIG. 2.

To package the λ phage DNA in vivo, γ protein encoded by the λ phage plays an important role. After injecting the λ phage DNA into the cytoplasm of a host cell, cos ends annealed and the λ DNA was circularized. At this point, so-called "Cairn's type" replication takes place. Once a sufficient amount of DNA is accumulated in the cell's cytoplasm, γ protein converted the replication from Cairn's to "rolling circle" replication for production of concatamers by inhibiting the activity of recBC protein. Then cos to cos packaging begins. Protein A, Nu-1 and other factors permits uptake of concatamers into λ phage heads and causes cleavage at the cos site. As a result, one molecule of λ DNA having open-cos sites at both ends is packaged into each λ phage head.

As explained above, λgtll and pHC79 are preferred for construction of the recombinant hybrid vector because:
1. Total size of cosmid should be as small as possible.
2. The location of cos site in cosmid vector should be almost the same distance from the cloning site (EcoRI site).
3. Each arm, when produced by cleaving at the cos site, should have a marker (e.g., an antibiotic resistance gene).
4. The cos region should be minimized to minimize the homologous recombination.
5. The origin of replication should be from ColE1 to be a relaxed type plasmid whose copy number can be controlled by chloramphenicol.

Extraction and EcoRI digestion of the hybrid DNA (i.e., forms A and B of FIG. 2) produce six fragments, the right arm of λgtll, the left arm of λgtll, intact λgtll DNA, linearized pHC79, the right arm of pHC79, and the left arm of pHC79. The fragments can be isolated by either gel electrophoresis, gel filtration, HPLC, or sucrose density gradient ultracentrifugation. In a preferred embodiment, the cos ends are treated with alkaline phosphatase, and then the λ DNA is digested with EcoRI. The digests are fractionated with either sucrose density gradient ultra-centrifugation or gel electrophoresis. The smallest two fragments are collected and purified. Only the cosR and cosL fragments resulting from the cosmid DNA (shown in fragment B of FIG. 2) are used in the present invention.

Use of Hybrid Vector Cos Arms to Transform Host With Foreign DNA

There are two main steps involved in this process, one is to prepare competent cells, and the other is to transform the cells with a desired foreign DNA segment using the cosmid arms produced from the above-described hybrid vector. These two main steps can be further broken down into the following specific steps.

Step 1: Preparation of competent cells

The host strain is inoculated in 10 mL of P medium (as shown in Kaiser et al. (15)) and then incubated at 37° C. until the $OD_{600}$ (optical density at 600 nanometers) reaches 0.5. The cells are chilled on ice, centrifuged, suspended in 5 ml of Medium 1 (also as shown in Kaiser et al. (15)), then the helper phage ($\lambda$cI857Sam7) is infected at m.o.i.=10. The cells are first incubated on ice for 10 min., then at 37° C. for 5 min., and then again on ice for 5 min.

To remove excess non-adsorbed phage, the cells are centrifuged, rinsed with 5 ml of ice-cold TMC (Tris-$Mg^{2+}$-$Ca^{2+}$ buffer, pH 7.0, containing 10 mM Tris HCl, 10 mM $MgCl_2$, and 10 mM $CaCl_2$), TM (Tris-$Mg^{2+}$ buffer) or a storage buffer, aliquoted in microfuge tubes and frozen in liquid nitrogen (when storage as frozen cells is desired).

Step 2: Preparation of Foreign DNA to be Transformed

Any known method of DNA preparation can be applied to prepare the foreign DNA that is desired to be transformed using the helper phage-mediated transformation method. There are several steps by which transformation efficiency can be optimized:
A. DNA extraction from the source;
B. DNA sizing (e.g., sonic treatment, partial digestion with restriction enzymes, exonuclease treatment, etc.);
C. DNA fractionation (sucrose density gradient ultracentrifugation, HPLC, gel electrophoresis, gel filtration);
D. end treatment with an exonuclease (e.g., ExoVII) when sonic treatment, or exonuclease treatment;
E. adaptor attachment: if the technique described in step D is used, adaptors which are complementary to the cloning site of the vector arms are ligated to the insert DNA. The short fragment of the adaptor DNA is phosphorylated but the longer fragment is not, thus avoiding concatamer formation of the adaptor DNA on the target DNA.
F. removal of non-ligated adaptor DNA: excess free adaptor DNA should be removed efficiently if the technique described in step E is used. If adaptor remains in the subsequent steps, it will inhibit efficient reactions. Gel filtration, gel electrophoresis, HPLC, or sucrose density gradient ultracentrifugation can be used for this purpose.

Step 3: Ligation of Foreign DNA Between Cosmid Arms

The foreign DNA described in step 2 is ligated between the cosmid arms described above in the section entitled "Production of Cosmid Arms from Hybrid Vector".

Step 4: Transformation

Competent cells (described above in step 1) which have been stored at −80° C. (when frozen cells are used) are thawed at 37° C. for 1.5 min. with gentle shaking. Ice-cold 10 mM Tris-HCl (pH 7.1) is added to the stock cells to dilute them five-fold, and the cells are chilled on ice. After precipitation, the cells are suspended in TM(C) ($2 \times 10^9$ ml) and kept on ice for 45 min. The ligated DNA (100 microliters) is mixed with 200 microliters of the competent cells on ice, then the mixture is incubated at 30° C. for 1 h to allow complete injection into the cytoplasm of the cell. The cells are spread onto a selective plate containing ampicillin and tetracycline. Roughly one transformation can be achieved with $10^3$ DNA molecules (26).

Example 1

Preparation of the Helper Phage

E. coli K-12 LE392 was infected with (helper) $\lambda$ phage $\lambda$cI857Sam7. LE392 was streaked on $\lambda$ broth and incubated at 37° C. overnight. Five colonies were selected and cultured in $\lambda$ broth at 37° C. overnight with aeration. With a loop, the stock of $\lambda$cI857Sam7 phage was streaked onto a $\lambda$ agar plate, and each culture was cross-streaked onto the same plate with a loop. After overnight incubation at 37° C., the cultures which had proper infectivity formed plaques. One E. coli strain was chosen, inoculated in $\lambda$ broth, and cultured at 37° C. overnight. 500 microliters of the LE392 bacterial strain was infected with 1 microliter of the stock $\lambda$ phage ($10^{10}$ pfu/ml) at room temperature for 15 min., and then transferred to 5 ml of fresh $\lambda$ broth. The infected strain was grown at 37° C. with shaking (275 rpm) until the culture became transparent by lysis. This took about 6 hours. Chloroform (100 microliters) was added to the culture and centrifuged for 10 min. at 4° C. to collect the supernatant (phage stock). This stock phage showed a titer ranging from $1 \times 10^8$ to $1 \times 10^9$ pfu/ml typically.

Phage-lysogenized E. coli cells were also prepared in the following way. The E. coli freshly prepared overnight culture (LE392, 200 microliters) was poured onto a $\lambda$ agar plate with 10 microliters of phage ($\lambda$cI857Sam7, diluted to $10^4$/ml) in 4 ml of $\lambda$ soft agar, and incubated at 30° C. overnight. The plates under this condition usually become confluent while the E. coli strain lysogenized with $\lambda$ phage will make colonies. The plate showed 22 colonies.

The lysogen (KD9301) was selected and cultured in 5 ml of $\lambda$ broth at 30° C. overnight. 200 microliters of the overnight culture was inoculated in 5 ml of fresh $\lambda$ broth, and cultured at 30° C. for about 4 hours until the $OD_{600}$ reached 0.5. The culture was transferred to a 42° C. water bath to inactivate the cI repressor which is a temperature sensitive repressor. Then, the culture was shaken at 42° C. for another 5 h. The culture was centrifuged to precipitate the cells, and suspended in 500 microliters of TM. Chloroform (100 microliters) was added to the culture to lyse the cells, which were then centrifuged to remove the cell debris. The supernatant showed a titer ranging from $1 \times 10^{10}$ to $1 \times 10^{11}$ pfu/ml typically.

Isolation of the Foreign DNA to be Transformed

For the foreign DNA to be transformed, DNA of $\lambda$KAD93.4 was selected. $\lambda$KAD93.4 DNA was extracted from a phage lysate and isolated at a concentration of 0.2 micrograms/ml.

Transformation of Host Bacterial Strain

The E. coli strain NS428 was grown overnight at 30° C. to prepare a fresh culture, The overnight culture (50 microliters) was inoculated in 5 ml of broth, and shaken at 30° C. until $OD_{600}$ reached 0.8 after about 4 hours. The cells were harvested by centrifugation, suspended in 2 ml of ice cold TM buffer, and stored on ice. The cells were mixed with the helper phage at m.o.i=10 on ice, and incubated on ice for 10 min. The mixture was incubated at 30° C. for another 10 min. to allow phage DNA injection, and ice cooled for one min.

Ice-cold TM (500 microliters; 10 mM Tris-HCl, pH 7.0–10 mM MgCl$_2$) was added to the mixture, and centrifuged at 4° C. for 1 min. to remove the non-infected phage. The cell pellet was then suspended in 200 microliters of ice-cold TMC (10 mM Tris-HCl, pH 7.0, 10 mM MgCl$_2$, 10 mM CaCl$_2$), and stored on ice until used. To these competent cells (200 microliters), 0.1 microgram of λKAD93.4 DNA in TE (Tris-EDTA buffer: 10 mM Tris-HCl at pH 8.0 plus 1 mM EDTA at pH 8.0) was added on ice after incubation at 70° C. for 10 min. to dissociate the cos ends from self-annealing. The mixture was then incubated on ice for 10 min. to allow the cos ends to anneal. The mixture was incubated at 30° C. for 30 min. with gentle swirling, and 1 microliter of 10 mg/ml DNase I was added to digest the rest of the DNA for transformation. One ml of LB broth (Luria-Bertani broth) was added to the mixture. The culture was incubated with shaking at 30° C. for 1.5 h, then spread (100 microliters) onto an LB agar plate with ampicillin (100 micrograms/ml) and tetracycline (25 µg/mL). The plates were incubated at 30° C. overnight. The colonies on the plates were counted and 6 randomly picked colonies were cultured in 5 ml of MMB (J. T. Baker Inc., Phillipsburg, N.J.) at 30° C. overnight. The transformation efficiency was about $5 \times 10^6$ cells/microgram DNA.

The resulting cultures were treated to extract the plasmid DNA with the SCREEN MAX MINI PLASMID extraction kit (available from J. T. Baker Inc.) or the PLASMID FAST kit (available from Amresco, Inc.).

Example 2

Construction of Hybrid Phage

The procedure shown in FIG. 2 was followed as discussed above and Fragment B (the open-cos cosmid arms) was isolated. The fragment can be isolated either by gel electrophoresis or sucrose density gradient ultracentrifugation.

To fractionate the open-cos arms, the two arms should be almost the same size. If they are not substantially the same size, the longer arm will migrate or sediment closely with the linear cosmid DNA on the gel or the sucrose density gradient, rendering recovery of the two arms difficult. In particular, the linear cosmid DNA which is a co-product from the hybrid phage DNA will contaminate the arms, because each fragment distributes according to the binomial distribution either on the gel or the sucrose density gradient. Therefore, the cos site of the cosmid should divide the EcoRI digested cosmid evenly to minimize contamination of the linear cosmid DNA. Currently, pHC79 is preferred for fulfilling this condition. Furthermore, since pHC79 is a pBR322 derivative, it is classified as relaxed type plasmid whose replication is independent of the host system resulting in stable plasmid maintenance due to its low copy number (up to 20 copies/cell) and easy amplification with either chloramphenicol or spectinomycin. Because plasmid segregation or rearrangement is likely when there is a long insert DNA and/or a high copy number, the plasmid should have a low copy number when it is maintained, but can be amplified when it is to be extracted. This is an advantage of the present invention over the BAC system. In addition, since two antibiotic resistance genes locate separately on each arm, unexpected rearrangements can be eliminated when the clones are grown on a medium with both antibiotics. Rearrangement may occur between the segments near the cos site locating apart after the passenger DNA is inserted, and homologous recombination may take place. Ampicillin and tetracycline resistance genes located on each arm of pHC79 can segregate the deleted plasmids which have lost one of the antibiotic resistance genes as well as the passenger DNA.

A lambda phage vector, λgt11 (24), and cosmid DNA, pHC79 (25), were digested with EcoRI, purified and ligated. The resulting DNA was then packaged in vitro into lambda heads (26), and infected into the proper host strain to allow in vivo packaging.

Generated phage were transferred onto a nylon membrane, and screened with a probe (pHC79). Positive phage were cultured independently and DNA extracted. Five clones were identified as a hybrid phage by restriction enzyme analysis, and one clone (λKAD93.4) was selected as a vector-arms producing phage, because the other four were hard to isolate DNA from due to their poor growth rate. Since the intensity of each band was almost proportional to its size, in vivo packaging occurred at almost equal rates for both possible patterns as shown in FIG. 2.

Those arms were then isolated from agarose gel, and tested for the ability to anneal to each other. At a 42° C. incubation in the presence of 20 mM MgCl$_2$, the two arms created a new large fragment (6.4 kb) which migrated the same as the linearized pHC79 DNA on an agarose gel. Then, this fraction was ligated and transformed into E. coli cells (SURE competent cells from Stratagene). All plasmid DNA examined (from 24 colonies) showed the EcoRI sites were intact by EcoRI digestion indicating that the recovered arms from the hybrid phage had the expected structure for HPMT.

Conditions for HPMT

Conditions for HPMT were optimized using the λKAD93.4 DNA fraction as a transforming DNA, λcI857Sam as a helper phage and NS428 (N205recA1) (λcI857 Aam11 Sam7 b2 red3) as a host strain. Since this DNA fraction includes a cosmid inside or outside the DNA with open cos sites, the total DNA fraction includes a cosmid inside or outside the DNA with open cos sites, the total DNA fraction is sufficient to test its ability or to optimize conditions for HPMT. It is likely that vast recombination will occur to the resulting transformants due to the repeated structure of lambda DNA.

Figure 4:
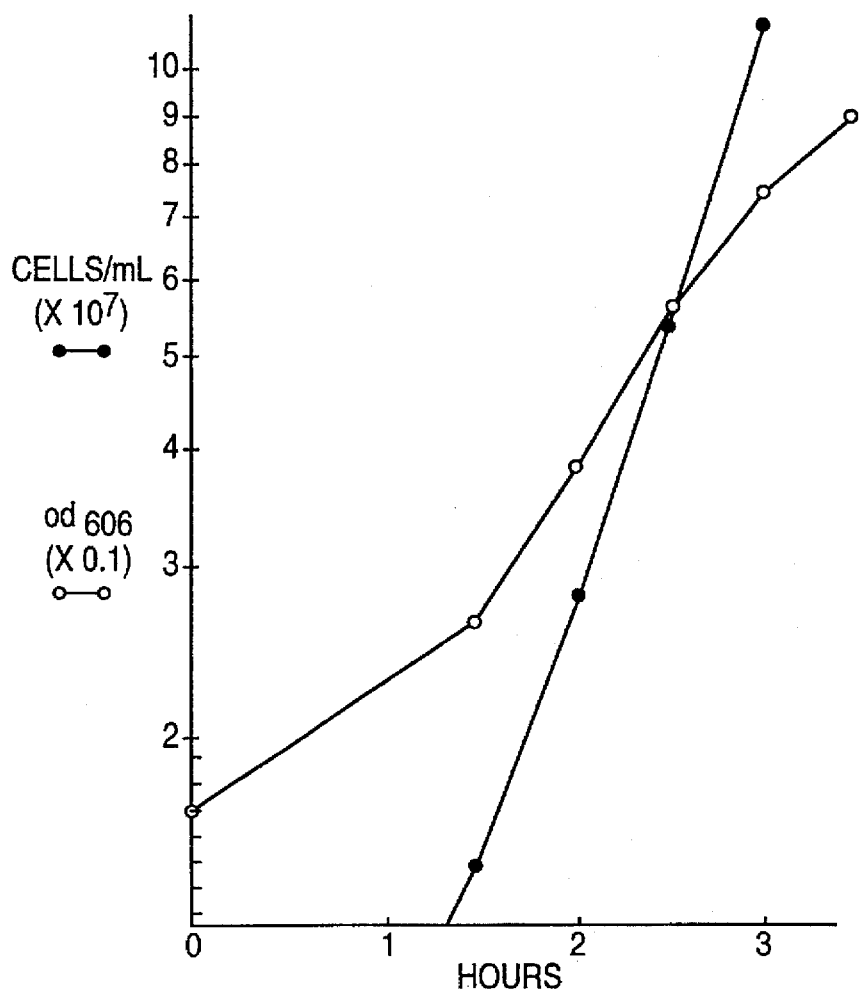
FIG. 4 shows the relationship between optical density at 600 nm ($OD_{600}$) and viable cell number for the NS428 strain.

At first, cell growth of the NS428 strain was examined to determine the relationship between optical density at 600 nm (OD$_{600}$) and viable cell number (FIG. 4). Based on the results, a 2.5 h cell culture in LB was used for subsequent tests, because the culture was estimated to be $5 \times 10^7$ cells/mL when the OD$_{600}$ was 0.5. Then, the cells were treated as in Ref. (18).

Figure 5:
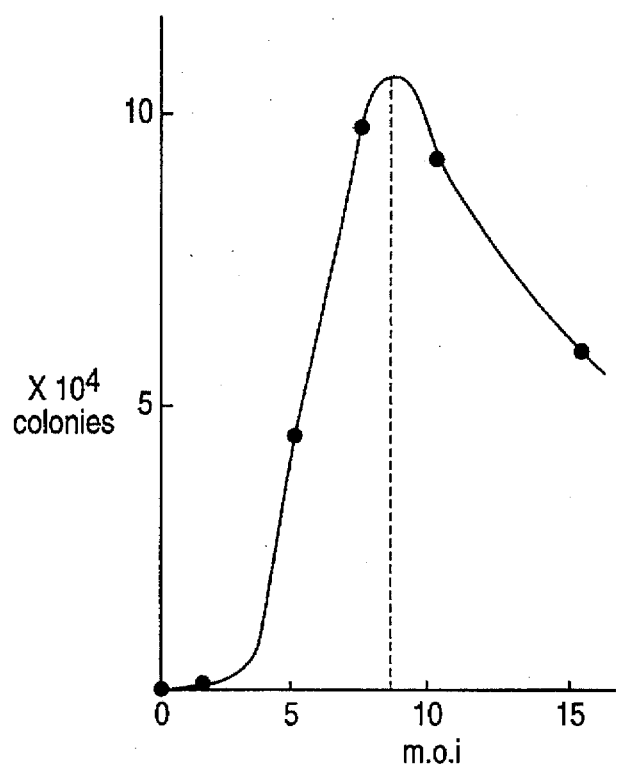
FIG. 5 shows multiplicity of infection (m.o.i.) plotted against number of colonies when competent cells were infected with λKAD93.4.

Multiplicity of infection (m.o.i.) was then optimized as shown in FIG. 5. The competent cells were mixed with λKAD93.4 DNA, transformed, and the colonies scored. The best m.o.i. was around 8.

To determine the linearity of transformation with increasing DNA concentration, HPMT was carried out changing the DNA concentration from 0.5 to 11 µg at m.o.i.=8. The results are shown in the following Table 1:

TABLE 1

| colonies | DNA (µg) | Efficiency (colonies/µg) |
| --- | --- | --- |
| 37° C. | | |
| 4260 | 0.272 | $1.57 \times 10^4$ |
| 5820 | 0.544 | $1.07 \times 10^4$ |
| 5720 | 1.088 | $5.26 \times 10^3$ |

TABLE 1-continued

| colonies | DNA (μg) | Efficiency (colonies/μg) |
|---|---|---|
| 8490 | 2.72 | $3.12 \times 10^3$ |
| 11150 | 5.44 | $2.05 \times 10^3$ |
| 30° C. | | |
| 7480 | 0.272 | $2.75 \times 10^4$ |
| 9950 | 0.544 | $1.83 \times 10^4$ |
| 6670 | 1.088 | $6.22 \times 10^3$ |
| 7250 | 2.72 | $2.67 \times 10^3$ |
| 11850 | 5.44 | $2.18 \times 10^3$ |

Figure 6:
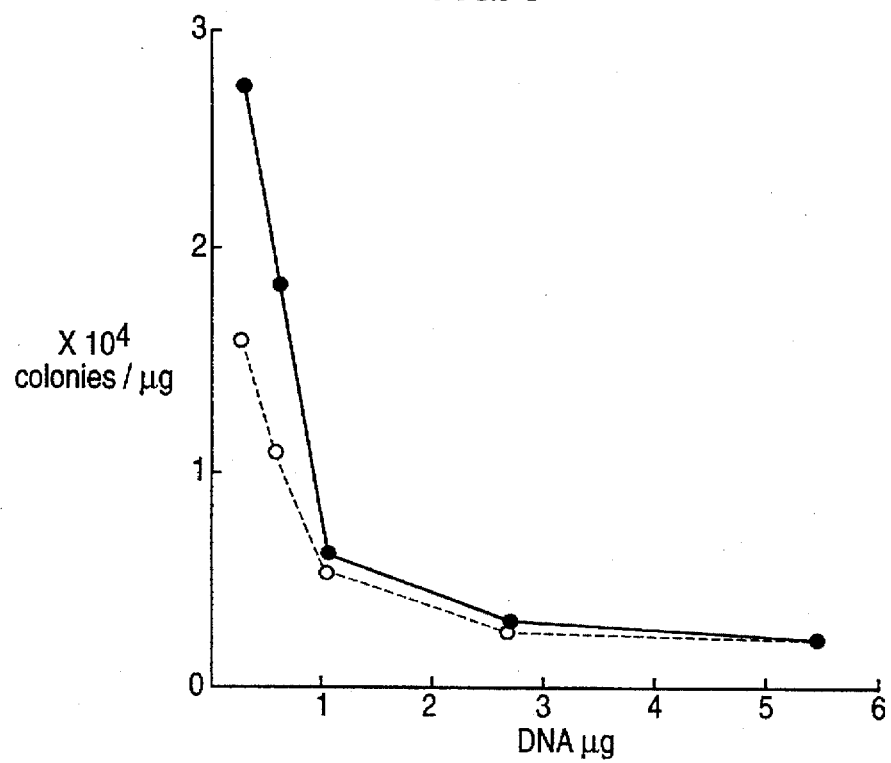
FIG. 6 shows transforming efficiencies plotted against the DNA amount.
Figure 7:
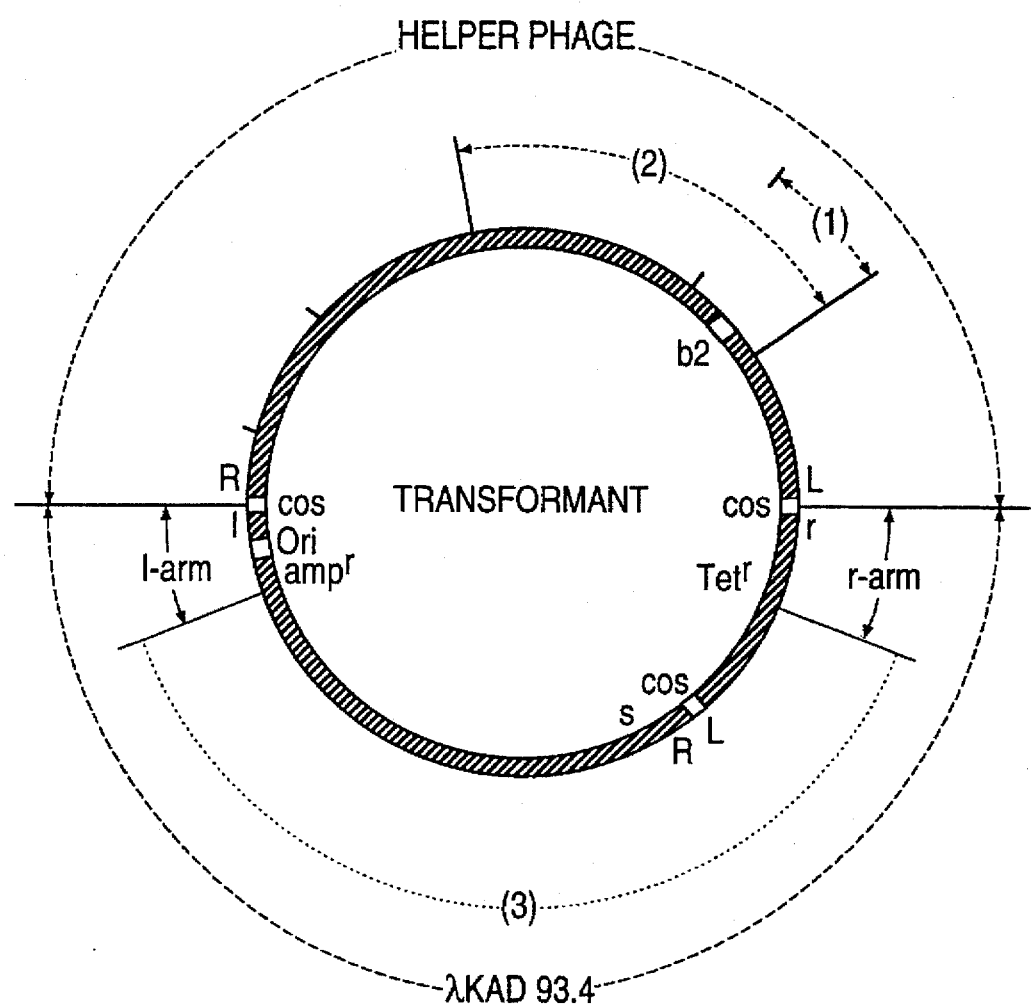
FIG. 7 shows a DNA map of a transformant obtained according to the present invention.
Figure 8:
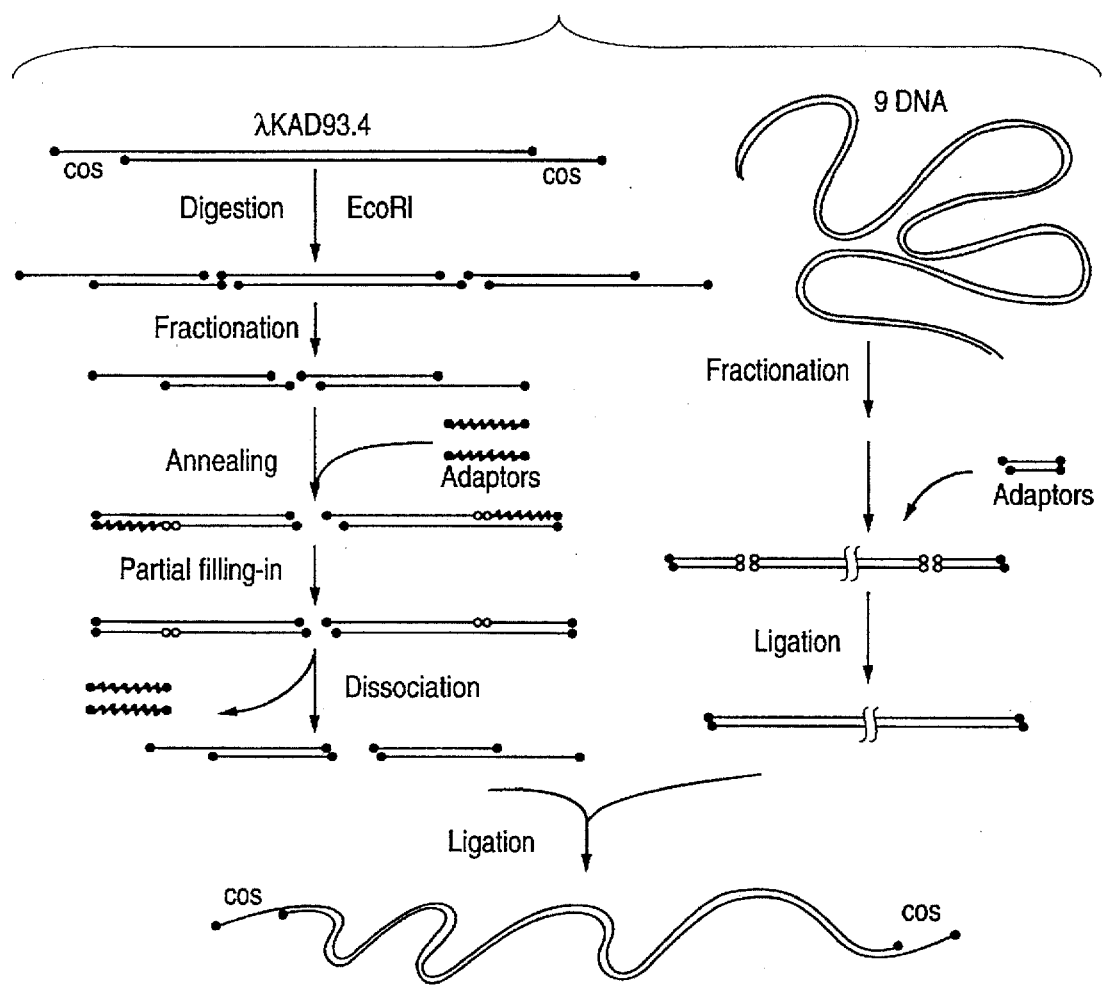
FIG. 8 shows the general method by which a fraction of foreign genomic DNA is ligated between the cos arms obtained from the hybrid vector of the present invention.

These results show a maximum transformation efficiency of $1.57 \times 10^4$ colonies/μg DNA, which is almost two orders of magnitude higher than Ref. (20) ($5.15 \times 10^2$ colonies/μg DNA). This may result from the number of open-cos sites in the presently invention. The authors of Ref. (20) did not confirm the ter reaction during transformation, further showing the higher efficiency of the present invention. As well as the regular conditions at 30° C., a non-permissive temperature (37° C.) was tested. It is noted that more colonies appeared when less DNA was used. When transforming efficiencies are plotted with the DNA amount, the curves match a typical rectangular hyperbola as shown in FIG. 6. This indicates that annealing between the helper phage DNA and the λKAD93.4 DNA occurred quite efficiently and annealing may contribute more than the chance of collision between cos sites. At the non-permissive temperature that may cause cell lysis, the efficiency was lower than at the permissive temperature.

All transformants obtained above showed vast levels of recombination. This is because the DNA used had the same segments from lambda phage and the expected recombinant included the helper phage DNA, and recombination was induced, probably at the initial stage of transformation, because the structures were stable once it established. This suggests that recombination is independent from the recA related homologous recombination system. This recombination may be minimized by shortening the cos region in pHC79 or improving the host strain using different rec mutations. The following table lists some of the strain names and corresponding genotypes for the strains referred to in the above description:

| strain name | genotype |
|---|---|
| KD9302 | mcrAΔ(mcrCB-hsdSMR-mrr)171, sbcC, rec J, rec B, uvrC, umuC::Tn5(kan')supE44, lac, gyrA96, relA1, thi-1, endA1, [F' proAB lacI^qZΔM15Tn10(tet^r)], λind- lysogen |
| KD9402 | same as KD9301 except F' minus |
| LE392 | mcrA, hsdR514, supE44, supF58, lacY1, Δ(lacIZY)6, galK2, galT22, metB1, trpR55 |
| λ$_{cI857Sam78}$ | Repressor is temperature sensitive. Lysozyme subunit is amber mutated. |
| λind- | Induction minus mutant. |
| λKAD93.4 | A hybrid phage of cosmid (pHC79) and bacteriophage λgt11. |
| KD9301 | LE392(λcI857Sam7) |

While the invention has been described in detail and with reference to specific embodiments thereof, it will be apparent to one skilled in the art that various changes and modifications can be made therein without departing from the spirit and scope of the invention.

LIST OF REFERENCES CITED

1. Laughon et al., Mol. Cell Biol., 6(1986):4676.
2. Strocher et al., id. at 4667.
3. O'Connor et al., EMBO J., 7(1988):435.
4. Kornfeld et al., Genes Dev., 3(1989):243.
5. Robertson, Nature, 327(1987):372.
6. Gitschier et al., Nature, 312(1984):326.
7. Peifer et al., Genes Dev., 1(1987):891.
8. Grosveld et al., Cell, 5(1987):975.
9. Spradling, Drosophila: A Practical Approach, (IRL Press, Oxford 1986), pp. 175–197.
10. Fire, EMBO J., 5(1986):2673.
11. Sambrook et al., Molecular Cloning: A Laboratory Manual, 2nd ed., Cold Spring Harbor Laboratory Press, New York (1989).
12. Sternberg, Proc. Natl. Acad. Sci., USA, 87(1990):103.
13. Burke et al., Science, 236(1987):806.
14. Shizuya et al., Proc. Natl. Acad. Sci., USA, 89(1992):8794.
15. Kaiser et al., J. Mol. Biol., 2(1960):392.
16. Kaiser, id., 4(1962):275.
17. Radding et al., id., 7(1963):225.
18. Kaiser et al., id., 13(1965):78.
19. Mandel, Mol. Gen. Genet., 99(1967):88.
20. Miller et al., Virology, 109 (1981):379.
21. Elliott et al., Mol. Gen. Genet., 161(1978):1.
22. Freifelder et al., Virology, 74(1976):169.
23. Becker et al., Proc. Natl. Acad. Sci., USA, 75(1978):4199.
24. Young et al., Proc. Natl. Acad. Sci., USA, 80(1983):1194.
25. Hohn et al., Gene, 11(1980):291.
26. Sternberg et al., id., 1(1977):255.
27. Kadokami et al., BioTechniques, 17(1994):580.

What is claimed is:

1. A method of transforming a host bacterial cell with a foreign DNA sequence comprising:

digesting λ phage vector DNA with a restriction enzyme to generate a left arm and a right arm, linearizing a cosmid vector with the restriction enzyme to produce linearized cosmid DNA, ligating the linearized cosmid DNA between the left and right arms to produce a hybrid phage-cosmid vector, packaging the hybrid phage-cosmid vector into phage heads in vitro, infecting a bacterial cell with the phage particles to propagate the phage particles thereby forming phage plaques, transferring the plagues onto a membrane, screening the hybrid phage-cosmid vector from the membrane by hybridizing with a DNA probe, preparing a phage lysate by infecting a bacterial cell with the hybrid phage-cosmid vector, precipitating the cell debris from the lysate, removing the bacterial cell's DNA and RNA by nuclease treatment, precipitating the propagated phage particles, extracting the packaged DNA from the precipitated phage particles, digesting the extracted DNA with the restriction enzyme which may or may not be the same as the first restriction enzyme to generate a mixture of DNA fragments, isolating the shortest two fragments from the mixture of fragments, each of which contains contain an open cos site on one end, ligating a foreign DNA sequence between the open cos fragments, and transforming a host bacterial cell with the ligated foreign DNA sequence having the open cos sites using a helper phage-mediated transformation system.

2. The method of claim 1 wherein the hybrid phage-cosmid vector is identified on the membrane by hybridization with a labeled probe.

3. The method of claim 1 wherein the host bacterial cell is selected from the group consisting of E. coli NS428 (λred), E. coli KD9302, and E. coli KD9402.

4. The method of claim 1 wherein the phage is λgt11.

5. The method of claim 1 further comprising, prior to transformation, ligating adaptor ends to the foreign DNA.

6. The method of claim 5 further comprising, prior to ligation with the adaptor ends, treating the foreign DNA sequence with Exo VII to insure that the ends are blunted.

7. The method of claim 1 further comprising, prior to ligating the foreign DNA sequence, dephosphorylating the fragments containing the open cos sites to avoid concatamer formation during the ligation reaction.

8. The method of claim 5 wherein gel filtration, HPLC, gel electrophoresis or density gradient ultracentrifugation is used to remove the adaptor ends prior to ligation of the foreign DNA to the cosmid end arms.

9. A hybrid DNA vector comprising a linearized cosmid having a unique restriction enzyme site between 2 marker genes, wherein the linearized cosmid is ligated between left and right arms produced from digestion of λ phage vector DNA.

10. The vector of claim 9, wherein the cosmid is 3.3 kb in length.

11. The vector of claim 10 wherein the cosmid is pHC79.

12. The vector of claim 11 wherein the phage DNA is from λgt11.

13. A mixture of DNA fragments each comprising an open cos site on one end and a restriction enzyme site on the other end derived from restriction enzyme digestion of a hybrid DNA vector comprising a linearized cosmid between left and right arms of λ phage vector DNA.

14. A purified DNA fragment as claimed in claim 13 which is up to about 3.3 kb in length.

15. A purified DNA fragment as claimed in claim 14 wherein the cos site has the sequence 5' GGGCGGCGACCT 3' (SEQ ID NO:1).

16. A purified DNA fragment as claimed in claim 15 wherein the restriction enzyme site is EcoR1.

17. A purified DNA fragment as claimed in claim 16 which further comprises a marker gene.

18. A method of transforming a host cell with a foreign DNA sequence comprising:

digesting λ phage vector DNA with a first restriction enzyme to generate a left arm and a right arm, linearizing a cosmid vector with the first restriction enzyme to produce linearized cosmid DNA, ligating the linearized cosmid DNA between the left and right arms to produce a hybrid phage-cosmid vector, packaging the hybrid phage-cosmid vector into phage heads in vitro, infecting a cell with the phage particles to propagate the phage particles thereby forming phage plaques, extracting the packaged DNA from the propagated phage particles, digesting the extracted DNA with a second restriction enzyme which may or may not be the same as the first restriction enzyme to generate a mixture of DNA fragments, isolating the fragments from the mixture of fragments which contain an open cos site on one end, ligating a foreign DNA sequence between two open cos fragments, and transforming a host cell with the ligated foreign DNA sequence having the open cos sites using a helper phage-mediated transformation system.

19. A method of producing open cos fragments comprising:

digesting λ phage vector DNA with a first restriction enzyme to generate a left arm and a right arm, linearizing a cosmid vector with the first restriction enzyme to produce linearized cosmid DNA, ligating the linearized cosmid DNA between the left and right arms to produce a hybrid phage-cosmid vector, packaging the hybrid phage-cosmid vector into phage heads in vitro, infecting a cell with the phage particles to propagate the phage particles thereby forming phage plagues, extracting the packaged DNA from the propagated phage particles, digesting the extracted DNA with a second restriction enzyme which may or may not be the same as the first restriction enzyme to generate a mixture of DNA fragments, isolating the fragments from the mixture of fragments which contain an open cos site on one end.

20. The method of claim 19, wherein the isolating step includes the step of isolating the shortest two fragments from the mixture of fragments, each of which contains an open cos site on one end.

21. A purified open cos fragment obtainable by the method recited in claim 20.

22. A method of transforming a host cell with a foreign DNA sequence comprising:

ligating a foreign DNA sequence between open cos fragments of claim 21, and transforming a host cell with the open cos fragment-ligated foreign DNA sequence.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:

-continued ( A ) LENGTH: 12 base pairs
( B ) TYPE: nucleic acid
( C ) STRANDEDNESS: single
( D ) TOPOLOGY: linear ( x i ) SEQUENCE DESCRIPTION: SEQ ID NO:1:

GGGCGGCGAC CT                                                                                              1 2